United States Patent
Lawandy

[11] Patent Number: 6,100,973
[45] Date of Patent: Aug. 8, 2000

[54] METHODS AND APPARATUS FOR PERFORMING MICROANALYTICAL TECHNIQUES USING PHOTOLITHOGRAPHICALLY FABRICATED SUBSTRATES HAVING NARROW BAND OPTICAL EMISSION CAPABILITY

[75] Inventor: Nabil M. Lawandy, North Kingston, R.I.

[73] Assignee: Spectra Science Corporation, Providence, R.I.

[21] Appl. No.: 09/059,276

[22] Filed: Apr. 13, 1998

[51] Int. Cl.[7] .................................................. G01N 1/10
[52] U.S. Cl. ........................................................... 356/246
[58] Field of Search .................................. 356/244, 246; 436/805; 372/43

[56] References Cited

U.S. PATENT DOCUMENTS

| | | | |
|---|---|---|---|
| 5,028,109 | 7/1991 | Lawandy | 350/96.12 |
| 5,434,878 | 7/1995 | Lawandy | 372/43 |
| 5,448,582 | 9/1995 | Lawandy | 372/42 |
| 5,524,011 | 6/1996 | Lawandy | 372/22 |
| 5,625,456 | 4/1997 | Lawandy | 356/376 |
| 5,867,266 | 2/1999 | Craighead | 359/246 |

FOREIGN PATENT DOCUMENTS

WO 96/36436  11/1996  WIPO.

OTHER PUBLICATIONS

"Lab on a chip", Jeffrey Young, Forbes, Sep. 23, 1996, pp. 210–211.

*Primary Examiner*—Teresa M. Arroyo
*Assistant Examiner*—Robert E. Wise
*Attorney, Agent, or Firm*—Ohlandt, Greeley, Ruggiero & Perle, LLP

[57] ABSTRACT

A substrate (10) has a surface (10A) containing at least one photolithographically defined feature (12, 14A, 14B) for containing a gas or fluid of interest. The substrate further includes at least one region (10B) containing a selected optical gain medium in combination with scattering particles or sites for generating light having a desired wavelength in response to a pump source, such as a laser (20) or a lamp. The at least one region is optically coupled to the at least one photolithographically defined feature for illuminating a portion of the sample with the light having the desired wavelength. The substrate may be comprised of a glass, a polymer, or a semiconductor. In one embodiment at least one optical waveguide (16) is formed in the substrate for conveying light from the pump source to the region containing the gain medium and scatterers. In further embodiments of this invention the pump source can be integrated into the substrate as a laser diode (18A), as may at least one photodetector (18B) for detecting a presence of light emitted by or transmitted through the sample in response to said light having the desired wavelength. Wavelength encoded features can also provided on a sample plate and subsequently identified, as can beads used in combinatorial chemistry and other applications.

14 Claims, 4 Drawing Sheets

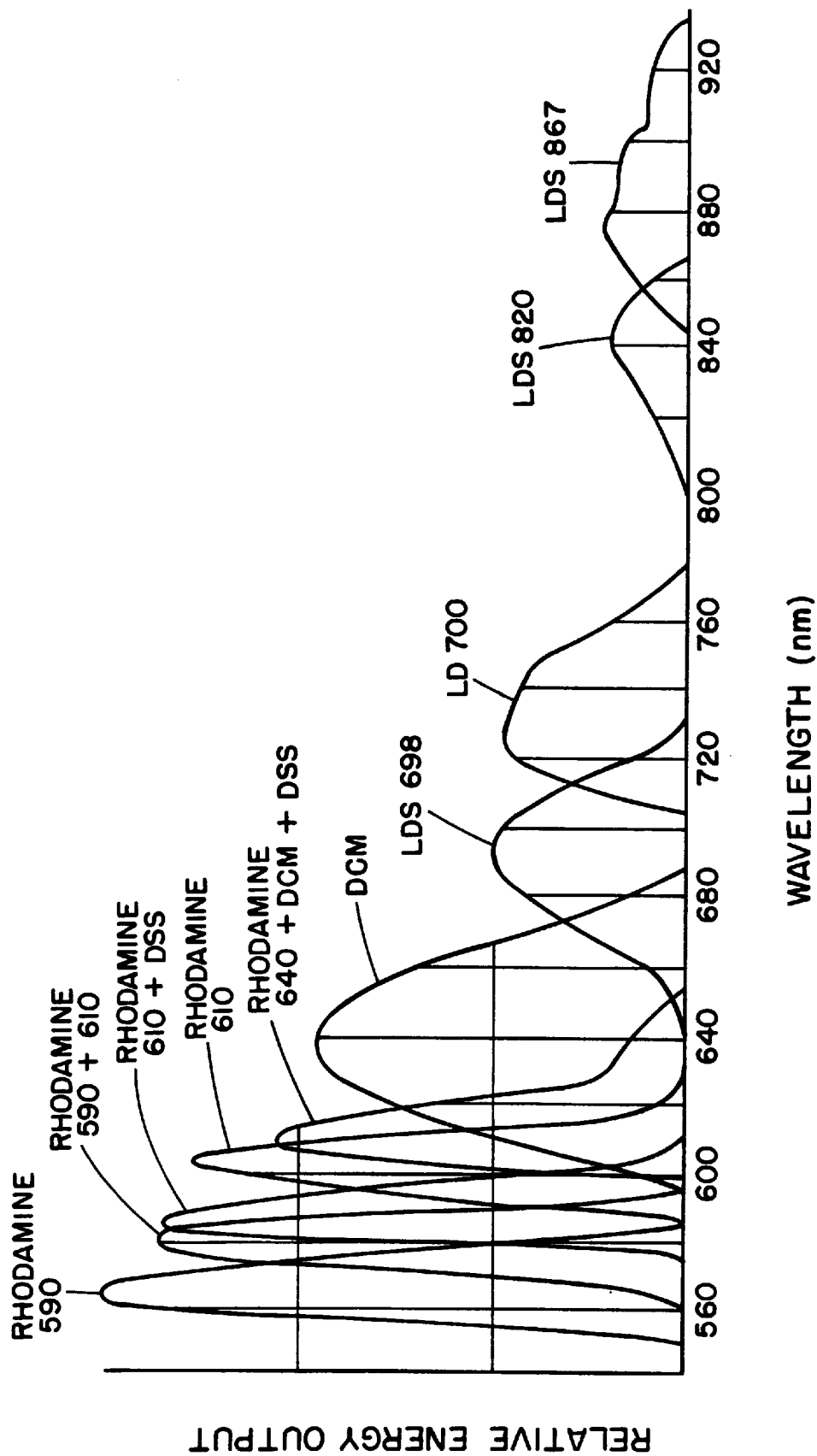

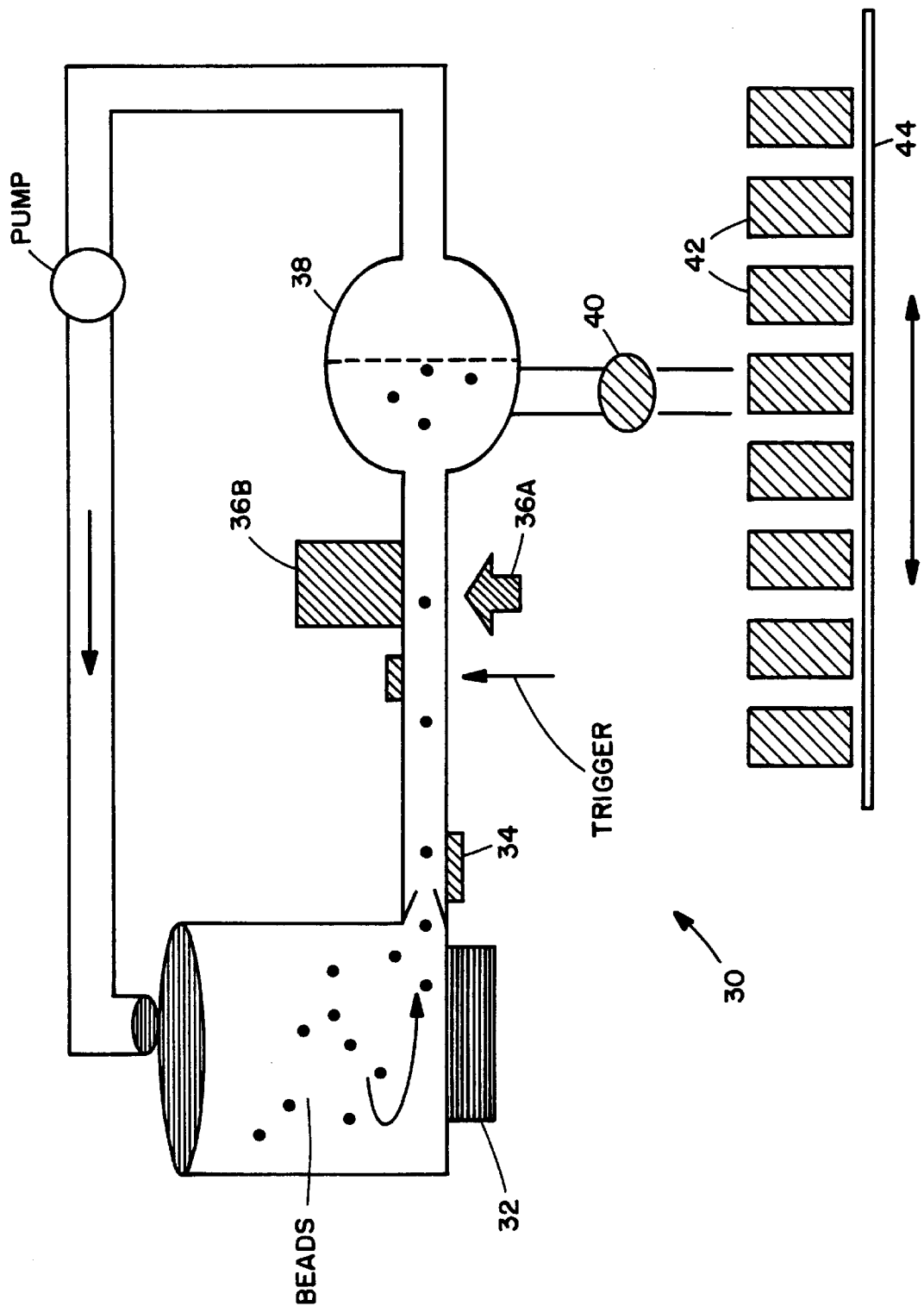

METHODS AND APPARATUS FOR PERFORMING MICROANALYTICAL TECHNIQUES USING PHOTOLITHOGRAPHICALLY FABRICATED SUBSTRATES HAVING NARROW BAND OPTICAL EMISSION CAPABILITY

CROSS-REFERENCE TO A RELATED PATENT APPLICATION

This patent application is related to copending U.S. patent application Ser. No.: 08/745,494, now U.S. Pat. No. 5,825,790 filed Nov. 12, 1996, which is a divisional patent application of U.S. patent application Ser. No.: 08/401,356, filed Mar. 9, 1995, now U.S. Pat. No. : 5,625,456, issued Apr. 29, 1997, which is a divisional patent application of U.S. patent application Ser. No.: 08/210,710, filed Mar. 18, 1994, entitled "Optical Sources Having a Strongly Scattering Gain Medium Providing Laser-Like Action", by Nabil M. Lawandy, now U.S. Pat. No. : 5,448,582, issued Sep. 5, 1995.

FIELD OF THE INVENTION

This invention relates generally to optically-based methods and apparatus for performing chemical and diagnostic testing of fluids and gases.

BACKGROUND OF THE INVENTION

In U.S. Pat. No. 5,448,582, issued Sep. 5, 1995, entitled "Optical Sources Having a Strongly Scattering Gain Medium Providing Laser-Like Action", the inventor disclosed a multi-phase gain medium including an emission phase (such as dye molecules) and a scattering phase (such as $TiO_2$). A third, matrix phase may also be provided in some embodiments. Suitable materials for the matrix phase include solvents, glasses and polymers. The gain medium is shown to provide a laser-like spectral linewidth collapse above a certain pump pulse energy. The gain medium is disclosed to be suitable for inclusion within glass and polymer substrate materials.

Recently there has been development in the field of miniaturized diagnostic testing apparatus, such as miniaturized capillary electrophoresis apparatus. One known approach uses photolithographic techniques to form sub-millimeter size channels and wells within a surface of a glass substrate. Fine metal electrodes are used to generate electric fields to move a fluid of interest through desired channels. Fluorescent markers can be added to the fluid which, when illuminated with light of certain wavelengths, emits a characteristic spectra. Photodetectors can then be used to detect the emission.

More particularly, the use of glass and plastic based microstructures has created a new field based on the miniaturization of bioanalytical processes. This includes clinical diagnostic applications, fabrication of oligonucleotide arrays and the electrophoretic separation of bio-molecules. Such microchip-based analytical systems may manipulate fluids using electro-kinetic, centrifugal and other transport mechanisms, and often use absorption and fluorescence techniques to determine and identify product species and sequences.

The use of such absorption and fluorescence techniques typically requires a precisely tuned narrow band optical pump source, such as a laser. If a wide variety of wavelengths are required a tuneable dye laser may be used. As can be appreciated, the use of dye lasers is typically less than desirable due to the initial cost, the recurring costs of upkeep and maintenance, and the required use of fluids, pumps and plumbing.

OBJECTS OF THE INVENTION

It is thus a first object of this invention to provide an improved method and apparatus for performing chemical diagnostic and other procedures using sample-handling substrates.

It is a further object of this invention to provide improved optically-based methods and apparatus for generating, in-situ, a plurality of desired narrow-band wavelengths for use in performing chemical diagnostic and other procedures using substrates having miniaturized gas or fluid-carrying channels, capillaries, and chambers.

SUMMARY OF THE INVENTION

The foregoing and other problems are overcome and the objects of the invention are realized by methods and apparatus in accordance with embodiments of this invention.

In accordance with this invention a substrate has a surface containing at least one photolithographically defined feature for containing a gas or fluid of interest. The substrate further includes at least one region containing a selected optical gain medium in combination with scattering particles or sites for generating light having a desired wavelength in response to a pump source, such as a laser or a lamp. The at least one region is optically coupled to the at least one photolithographically defined feature for illuminating a portion of the sample with the light having the desired wavelength. The substrate may be comprised of a glass, a polymer, or a semiconductor.

In one embodiment at least one optical waveguide is formed in the substrate for conveying light from the pump source to the region containing the gain medium and scatterers.

In further embodiments of this invention the pump source can be integrated into the substrate, as may at least one photodetector for detecting a presence of light emitted by or transmitted through the sample in response to said light having the desired wavelength.

Wavelength encoded features can also provided on a sample plate and subsequently identified, as can beads used in combinatorial chemistry and other applications, such as mix and split combinatorial synthesis applications.

BRIEF DESCRIPTION OF THE DRAWINGS

The above set forth and other features of the invention are made more apparent in the ensuing Detailed Description of the Invention when read in conjunction with the attached Drawings, wherein:

FIG. 6 illustrates a number of exemplary dyes that are suitable for practicing this invention;

FIG. 9 is a diagram of wavelength encoded sample bead fluidic sorting system.

DETAILED DESCRIPTION OF THE INVENTION

The disclosure of the above-referenced U.S. Pat. No. 5,448,582, issued Sep. 5, 1995, entitled "Optical Sources Having a Strongly Scattering Gain Medium Providing Laser-Like Action", by Nabil M. Lawandy is incorporated by reference herein in its entirety. Also incorporated by reference herein in its entirety is the disclosure of U.S. Pat. No. 5,434,878, issued Jul. 18, 1995, entitled "Optical Gain Medium Having Doped Nanocrystals of Semiconductors and also Optical Scatterers", by Nabil M. Lawandy.

This invention employs an optical gain medium that is capable of exhibiting laser-like activity when excited by a source of excitation energy, as disclosed in the above-referenced U.S. Patents. The optical gain medium is comprised of: a matrix phase, for example a polymer or glass, that is substantially transparent at wavelengths of interest; an electromagnetic radiation emitting and amplifying phase, for example a chromic dye or a phosphor; and a high index of refraction contrast electromagnetic radiation scattering phase, such as particles of an oxide and/or scattering centers within the matrix phase.

This invention employs the discovery by the inventor that a dye or some other material capable of emitting light, in combination with scattering particles or sites, exhibits electro-optic properties consistent with laser action; i.e., a laser-like emission that exhibits both a spectral linewidth collapse and a temporal collapse at an input pump energy above a threshold level.

The invention is applied herein to the construction of substrates having microchannels, capillaries, wells, chambers, and any other features suitable for flowing and/or containing a sample of a fluid or gas, wherein the substrate further includes at least one portion containing the gain medium and scatterers- for providing narrow-band (e.g., about 3 nm) optical radiation to a region of interest. In accordance with further embodiments of this invention the substrate may also include at least one laser diode for exciting the gain medium, and may include at least one photodetector for detecting an emission of the sample resulting from the activation of the gain medium. The photodetector can be used instead for detecting an amount of unabsorbed light from the gain medium that is transmitted through the sample.

Figure 1:
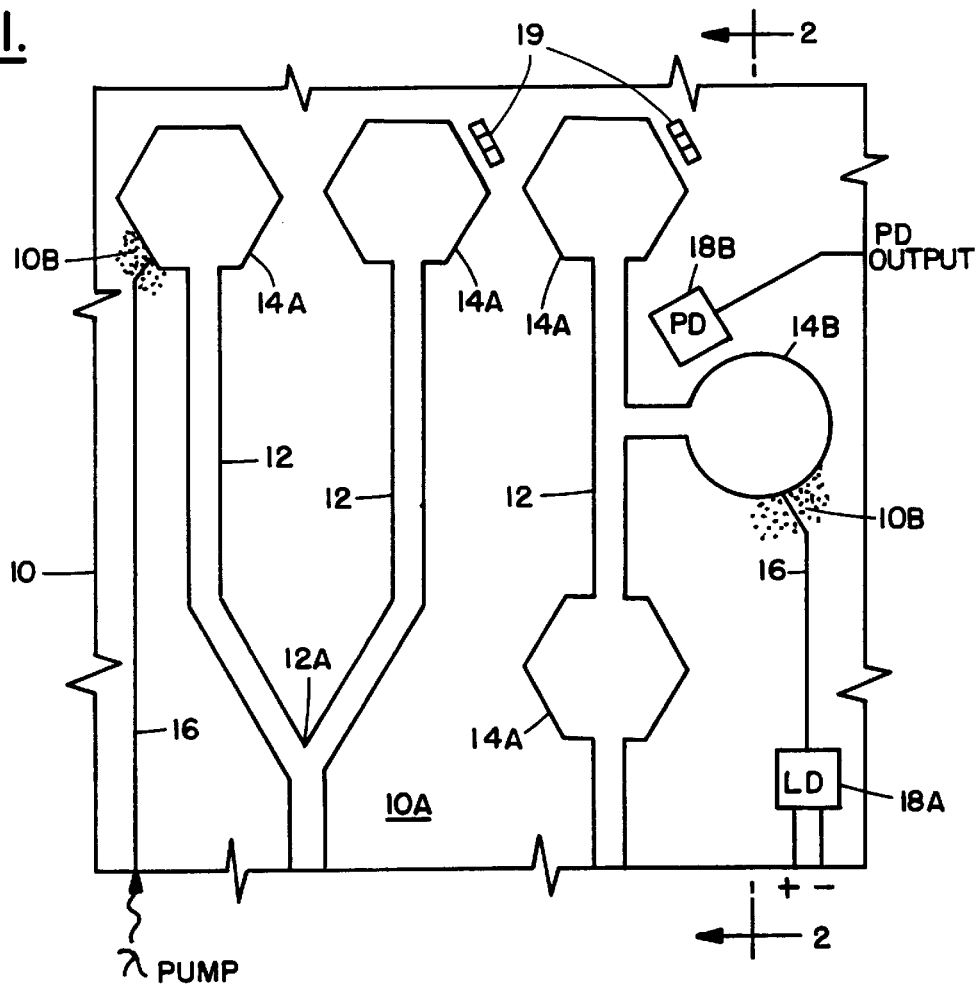
FIG. 1 illustrates an enlarged top view of a substrate having a surface that contains a plurality of features, such as channels and wells, through which a fluid of interest can be flowed during a microanalytical procedure, the substrate containing the gain medium and scatterers in accordance with this invention.
Figure 2:
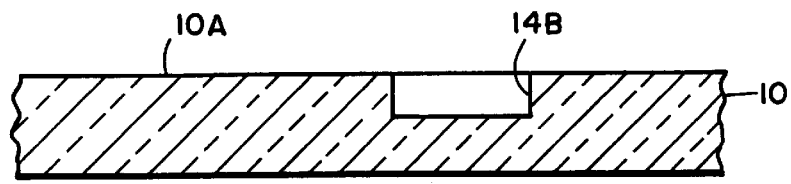
FIG. 2 is an enlarged cross-sectional view taken along the section line 2—2 of FIG. 1.

FIG. 1 illustrates an exemplary enlarged top view of a substrate 10 having a surface 10A that contains a plurality of features, such as channels 12 and wells 14A and 14B, through which a fluid of interest can be flowed during a microanalytical procedure. By example, the circular well 14B may have a diameter of a millimeter or less. FIG. 2 is an enlarged cross-sectional view taken along the section line 2—2 of FIG. 1, and shows in greater detail the circular well 14B. The substrate 10 may be comprised of a glass, a polymer such as a polycarbonate, or a semiconductor, such as silicon. Not shown in FIGS. 1 and 2 are any electrodes that may be used for establishing electric fields.

Figure 5:
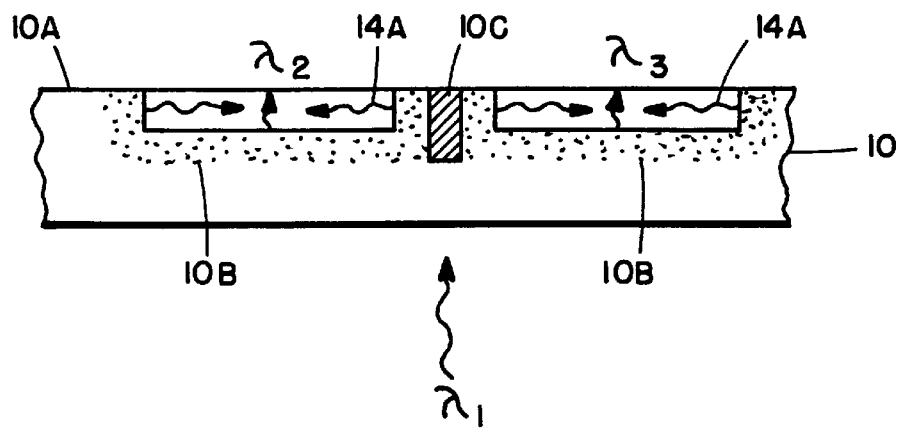
FIG. 5 is a cross-sectional view of an exemplary substrate in accordance with the teachings of this invention.

The particular arrangement of channels 12 and wells 14A and 14B in FIG. 1 is provided as an example only. In general, any suitable arrangement can be used for the intended application. A fluid or gas can be moved through and into the channels 12 and wells 14A and 14B using any suitable electro-kinetic, centrifugal and/or other transport mechanisms. It should be realized that a cover (not shown) may be placed over the surface 10A, such as a second glass or polymer substrate. In accordance with this invention the substrate 10 contains one or more selected types of gain medium and scatterers that are optically coupled to one or more of the features, such as through an intervening transparent portion of the substrate 10. Referring to FIG. 5, it can be seen that two exemplary wells 14A are each surrounded by a region 10B containing the optical gain medium (e.g., a selected dye or phosphor) and also scattering particles (e.g. $TiO_2$). When illuminated with light ($\lambda_1$) from a laser or lamp above a threshold fluence, each region 10B emits light at a wavelength determined by the selected gain medium. By example, one region can emit light into a first well 14A with a wavelength $\lambda_2$, while the other region emits light into a second well 14A with a wavelength $\lambda_3$. The regions 10B need not completely surround the well or channel (see, for example, the region 10B in FIG. 1), and the input pump light need not impinge on the bottom surface. The particular gain medium that is selected for a given well or channel is a function of the intended application. For example, if it is desired to activate a particular fluorescent marker that has an optimum sensitivity to a particular band of wavelengths, then the gain medium is selected accordingly to emit in or as near as possible to the particular wavelength band. If desired, an optical absorber or reflector 10C can be formed into the substrate 10 in order to optically isolate different portions from one another. By example, a reflector 10C can be formed by etching a channel to a desired depth, and then filling the channel with a metal, such as gold. An absorber can be formed by filling the channel with an oxide or any suitable opaque material.

FIG. 6 illustrates a number of exemplary dyes that are suitable for practicing this invention, and shows their relative energy output as a function of wavelength. The teaching of this invention is not limited for use with only the dyes listed in FIG. 6.

The regions 10B can be formed such as by etching or scribing a ring around a selected one of the wells, and then filling the ring with a selected gain medium in combination with selected scatterers. A linear feature can be likewise formed and subsequently filed with a selected gain medium and scatterer.

Figure 3:
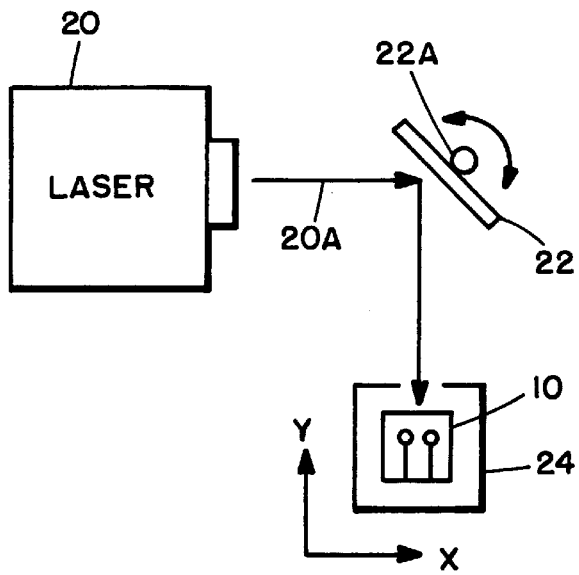
FIG. 3 illustrates one embodiment of an optical source for exciting the gain medium within the substrate.

FIG. 3 illustrates one embodiment of an optical source for exciting the selected gain medium(s) in the substrate 10. By example, a frequency doubled Nd:YAG laser 20 emits a pulsed output beam 20A. A mirror 22 is arranged to reflect the beam to the substrate 10. The substrate 10 may be positioned on a suitable X-Y translation stage 24 so that the beam 20A can illuminate different locations on the substrate 10. Alternatively, or in conjunction with the use of the translation stage 24, the mirror 22 may include an actuator 22A for scanning the mirror and hence the beams 20A over the substrate 10. One or more suitable photodetectors, not shown, can be arranged to detect the emitted light from illuminated channels, capillaries, wells or chambers of the substrate 10.

Figure 4:
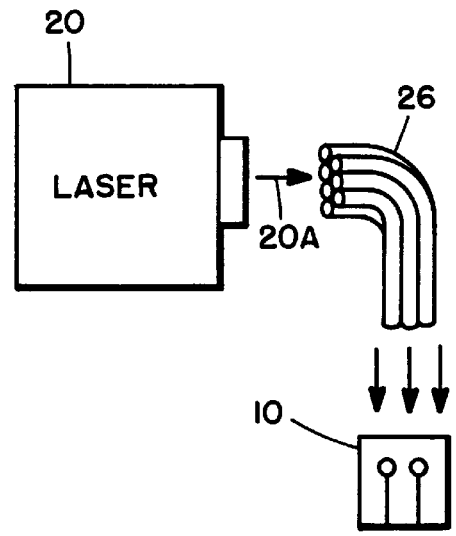
FIG. 4 illustrates another embodiment of an optical source for exciting the gain medium within the substrate.

FIG. 4 illustrates an embodiment wherein a fiber optic bundle 26 is used to convey the pump radiation from the laser 20 to the substrate 10. In this embodiment the individual fiber optics can be terminated at the substrate in a desired spatial pattern that corresponds to wells, channels and the like wherein it is desired to simultaneously provide the pump light. Alternatively, the fiber optic bundle 26 may simply replace the mirror 22 in the embodiment of FIG. 3.

Further in accordance with this invention, and referring again to FIG. 1, it is within the scope of the invention to integrate one or more optical channels or waveguides 16, and/or one or more pump sources, such as a laser diode 18A, and/or one or more photodetectors 18B into the substrate 10. In this manner optical pump radiation can be precisely delivered to a desired location, and/or emitted radiation can be detected in close proximity to the emitting source, such as fluorescent marker contained in one of the wells 14 or channels 12. The photodetector 18B can be used instead for detecting an amount of unabsorbed light from the gain medium region 10B that is transmitted through the sample contained in the well 14B.

In this embodiment any required electrical leads, such as power leads for the laser diode 18A and leads for the photodetector 18B, are also integrated into the substrate 10 and brought, preferably, to peripheral I/O pads. Laser light can also be input at the periphery of the substrate 10 and then conveyed by the waveguide 16 to one or more desired locations. For this particular embodiment of the invention it is preferred to construct the substrate 10 from or to include a semiconductor material, such as silicon or a Group III–V material, thereby facilitating the fabrication of laser diodes and/or photodetectors.

It is also within the scope of this invention, when using glass substrates, to provide optical waveguides that are capable of also frequency doubling the laser light passing therethrough. Reference in this regard can be had to FIGS. 13a and 13b of the inventor's earlier U.S. Pat. No. : 5,524,011. The disclosure of this U.S. Pat. No. is incorporated by reference herein in its entirety.

It is further within the scope of this invention, when using polymeric substrates, to also provide optical waveguides that are capable of frequency doubling the laser light passing therethrough. Reference in this regard can be had to the inventor's earlier U.S. Pat. No. : 5,028,109. The disclosure of this U.S. Pat. No. is also incorporated by reference herein in its entirety.

Figure 7:
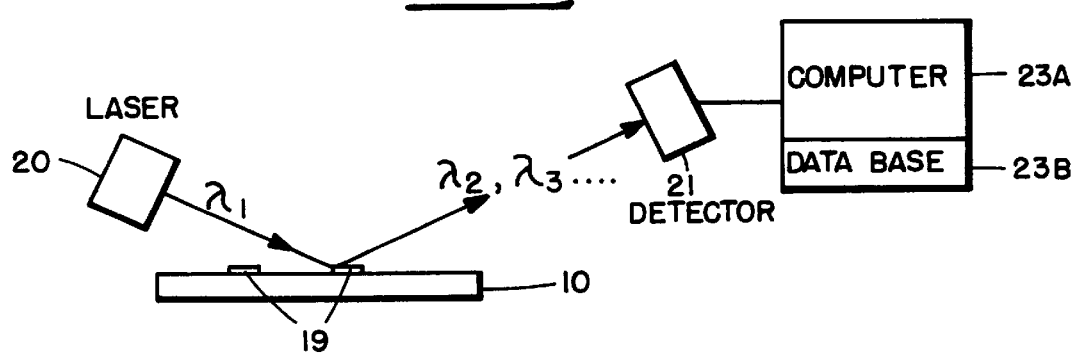
FIG. 7 is a block diagram of a system for reading optically encoded wells and/or other structures on a sample plate.

Further in accordance with an aspect of this invention the substrate 10 can be provided with one or more wavelength encoded regions 19 each comprised of one or more combinations of the gain medium and scatterers for identifying individual ones of the wells 14A, 14B, in addition to other structures of interest, such as branch points 12A in the channels 12. By providing the gain material such that multiple wavelengths are emitted, the system shown in FIG. 7 can be used to optically excite the regions 19, and then detect the resulting emission wavelength(s). Using a wavelength selective detector 21, a computer 23A is enabled to lookup the detected wavelength(s) in a database 23B for correlating the detected wavelength(s) with a specific well or structure on the substrate 10. It is also within the scope of this invention to so wavelength encode an identifier for the entire plate or substrate 10 so that individual substrates can be automatically identified and tracked.

Figure 8:
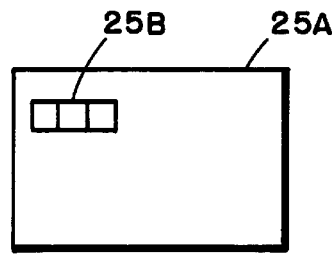
FIG. 8 is an enlarged view of an optically encoded bead that can be used with the sample plate.

As is shown in FIG. 8, it is further within the scope of this invention to wavelength encode individual beads 25A used for combinatorial chemistry applications by providing each bead with a region 25B comprised of gain medium and scatters. Combinations of narrow band (e.g., approximately 4 nm) laser emission signals can be thus used to create high density codes for combinatorial chemistry applications. For example, a library size of ($2^N$–1) different encodings can be provided with N distinct gain medium emitters (e.g., if N=20 then approximately $10^6$ different codes can be obtained).

FIG. 9 illustrates a wavelength encoded bead fluidic sorting system 30 wherein the wavelength encoded beads 25A (e.g., plastic beads of size 500–2000 microns) are carried by a fluid and are agitated 32, separated (e.g., ultrasonically) 34, optically decoded using a laser source 36A and a detector 36B after generating a trigger signal, concentrated 38, and provided through a valve 40 to individual reaction vessels 42 placed on a moving conveyor 44.

The beads 25A may also be used with the substrate 10 by being flowed through the channels 12 and accumulated in the wells 14A and 14B, or simply placed in the wells. In this case a system similar to that of FIG. 7 can be used to detect the locations of the beads 25A, and/or identify which bead(s) 25A are located in a given one of the wells 14A, 14B. Various reagents can be encoded in this way as well.

While the invention has been particularly shown and described with respect to preferred embodiments thereof, it will be understood by those skilled in the art that changes in form and details may be made therein without departing from the scope and spirit of the invention.

What is claimed is:

1. A substrate having a surface containing features for at least one of containing or flowing a gas or fluid of interest, said substrate further comprising at least one region containing a plurality of selected optical gain mediums in combination with scattering particles or sites for generating a laser-like emission having a plurality of predetermined wavelengths in response to a pump source, the at least one region being disposed in association with at least one of the features within the substrate such that a detection of said plurality of predetermined wavelengths identifies said at least one feature.

2. A substrate having a surface containing features for at least one of containing or flowing a gas or fluid of interest, said substrate further comprising a region containing selected optical gain mediums in combination with scattering particles or sites for generating a laser-like emission having a plurality of predetermined wavelengths in response to the pump source, wherein a detection of said plurality of predetermined wavelengths identifies said substrate.

3. A substrate having a surface wherein a plurality of features are disposed for containing a material of interest, said substrate comprising a plurality of regions each comprised of a selected optical gain medium in combination with scattering particles or sites for generating light having a desired wavelength in response to at least one pump source, individual ones of said Plurality of regions being optically coupled to at least one of said plurality of features for illuminating material contained within said at least one feature with the generated light having the desired wavelength, wherein at least two of said plurality of regions generate light having different wavelengths in response to said at least one pump source.

4. A substrate as set forth in claim 3, wherein said substrate is comprised of a glass.

5. A substrate as set forth in claim 3, wherein said substrate is comprised of a polymer.

6. A substrate as set forth in claim 3, wherein said substrate is comprised of a semiconductor.

7. A substrate as set forth in claim 3, and further comprising at least one optical waveguide for conveying light from said at least one pump source to individual ones of said plurality of regions.

8. A substrate as set forth in claim 3, wherein said at least one pump source is integrated into said substrate.

9. A substrate as set forth in claim 3, and further comprising at least one photodetector that is integrated into said substrate for detecting a presence of light emitted by said sample in response to said light having the desired wavelength.

10. A substrate as set forth in claim 3, and further comprising at least one photodetector that is integrated into said substrate for detecting a presence of light transmitted by said sample in response to said light having the desired wavelength.

11. A substrate as set forth in claim 3, and further comprising at least one optical absorber disposed between two adjacent one of said features.

12. A substrate as set forth in claim 3, and further comprising at least one optical reflector disposed in proximity to at least one of said features.

13. A substrate as set forth in claim 3, wherein at least one of said regions is disposed beneath a bottom surface of at least one feature, and is further disposed along at least one sidewall of said at least one feature for illuminating, simultaneously from a plurality of directions, said material contained within said at least one feature.

14. A substrate as set forth in claim 3, wherein at least one of said plurality of features is formed such that it is disposed within at least one of said plurality of regions.

* * * * *